United States Patent
Mengler

(10) Patent No.: US 10,646,439 B2
(45) Date of Patent: May 12, 2020

(54) AQUEOUS PHARMACEUTICAL FORMULATION COMPRISING PROPOFOL

(71) Applicant: Cuda Anesthetics, LLC, Douglas Manor, NY (US)

(72) Inventor: Christopher Mengler, Douglas Manor, NY (US)

(73) Assignee: Cuda Anesthetics, LLC, Douglas Manor, NY (US)

( * ) Notice: Subject to any disclaimer, the term of this patent is extended or adjusted under 35 U.S.C. 154(b) by 0 days.

(21) Appl. No.: 16/073,580

(22) PCT Filed: Jan. 25, 2017

(86) PCT No.: PCT/US2017/014909
§ 371 (c)(1),
(2) Date: Mar. 19, 2019

(87) PCT Pub. No.: WO2017/132243
PCT Pub. Date: Aug. 3, 2017

(65) Prior Publication Data
US 2019/0060232 A1    Feb. 28, 2019

Related U.S. Application Data

(60) Provisional application No. 62/288,671, filed on Jan. 29, 2016.

(51) Int. Cl.
*A61K 31/045* (2006.01)
*A61K 9/08* (2006.01)
*A61K 31/05* (2006.01)
*A61K 31/724* (2006.01)
*A61P 23/00* (2006.01)
*A61K 9/00* (2006.01)
*A61K 47/12* (2006.01)
*A61K 47/40* (2006.01)

(52) U.S. Cl.
CPC ............. *A61K 9/08* (2013.01); *A61K 9/0019* (2013.01); *A61K 31/05* (2013.01); *A61K 31/724* (2013.01); *A61K 47/12* (2013.01); *A61K 47/40* (2013.01); *A61P 23/00* (2018.01)

(58) Field of Classification Search
CPC ................................................... A61K 31/045
USPC ........................................................ 514/730
See application file for complete search history.

(56) References Cited

U.S. PATENT DOCUMENTS

2003/0073665 A1* 4/2003 Thompson ........... A61K 9/0019
514/58

* cited by examiner

*Primary Examiner* — Raymond J Henley, III
(74) *Attorney, Agent, or Firm* — Sterne, Kessler, Goldstein & Fox, P.L.L.C.

(57) ABSTRACT

Disclosed herein is an aqueous pharmaceutical formulation comprising about 10 mg/mL of propofol, 175 mg/mL of sulfobutylether β-cyclodextrin, a citric buffer, wherein the composition has a pH of about 5.5. Also disclosed is a method of inducing and maintaining anesthesia or sedation in a patient by administering the aqueous pharmaceutical formulation.

20 Claims, No Drawings

AQUEOUS PHARMACEUTICAL FORMULATION COMPRISING PROPOFOL

BACKGROUND OF THE INVENTION

Propofol (2,6-diisopropylphenol or 2,6-bis(1-methylethyl)-phenol)) is an anesthetic agent for use in the induction and maintenance of anesthesia or sedation. Propofol is formulated in an oil-in-water emulsion for intravenous injection due to its poor water solubility. For example, Diprivan® is an oil-in-water emulsion comprising propofol, soybean oil, and egg lecithin approved by the FDA in 1989. These emulsion products have many undesirable attributes. Many patients complain of moderate to severe pain upon injection. The fatty components of the emulsion, such as egg lecithin, pose an allergic risk to some patients. Emulsions are difficult to sterilize by autoclave or filtration, so these products are not considered to be antimicrobially preserved under USP standards. As such, strict aseptic techniques must be maintained during handling to decrease the risk of microbial contamination, and consequent infection in patients. These issues and additional manufacturing difficulties have resulted in several recalls of propofol emulsions and a long-term drug shortage.

Modifications to the emulsion formulations comprising propofol have been made. For instance, antimicrobial agents such as benzyl alcohol and sodium benzoate are included in emulsion products to reduce microbial contamination, e.g., U.S. Pat. Nos. 6,140,374 and 6,147,122. However, these antimicrobial agents can cause toxicity, especially at high concentration. Also, attempts have been made to reduce injection site pain by raising the pH of the emulsion to above pH 6.5, e.g., U.S. Pat. No. 8,546,453.

Efforts have been made to develop non-emulsion propofol products in view of the undesirable attributes associated with the emulsion products and supply shortage. For example, U.S. Pat. No. 7,034,013 relates to a non-emulsion propofol product comprising propofol, cyclodextrin such as sulfobutyl ether β-cyclodextrin, and water, as well as other excipients. It was also known that the amount of sulfobutyl ether β-cyclodextrin is preferably in the range of 18-20% or more for a 10 mg/mL propofol solution so the drug remains in solution during manufacturing and storage. The excess amount of sulfobutyl ether β-cyclodextrin was believed to reduce injection site pain. However, despite such efforts, development of non-emulsion propofol products has not been successful. Diprivan® and its generic counterparts remain the only FDA-approved propofol products today.

BRIEF SUMMARY OF THE INVENTION

The invention features an aqueous pharmaceutical formulation comprising propofol, sulfobutylether β-cyclodextrin, citric acid, and has a pH of about 5.5. The aqueous formulation reduces or eliminates the undesirable attributes, such as allergic reactions, lipid overload, and microbial contamination, associated with known emulsion products. It also significantly reduces manufacture difficulties associated with emulsion products and consequently, relieves supply shortage.

In one embodiment, the invention features an aqueous pharmaceutical composition comprising about 10 mg/mL of propofol and 175 mg/mL of sulfobutylether β-cyclodextrin, and has a pH of about 5.5. In one embodiment, the composition comprises about 10 mg/mL of propofol and 175 mg/mL of sulfobutylether β-cyclodextrin, and has a pH of about 5.5. In one embodiment, the pH of the composition is adjusted with a buffer such as an acetate buffer, a citrate buffer, a phosphate buffer, a lactate buffer, or a tartrate buffer, preferably a citrate buffer. In a further embodiment, the composition further comprises acetic acid, citric acid, phosphoric acid, ascorbic acid, tartaric acid, succinic acid, adipic acid, or malic acid, preferably, citric acid. Preferably, the sulfobutylether β-cyclodextrin in the aqueous pharmaceutical composition is sulfobutylether 7β-cyclodextrin, sulfobutylether 4β-cyclodextrin, or a combination thereof. More preferably, the sulfobutylether β-cyclodextrin is Captisol®.

In one embodiment, the aqueous pharmaceutical composition further comprises a preservative, an antioxidant, a tonicity modifier, an additional solubilizing agent, or a combination thereof.

In one embodiment, the aqueous pharmaceutical composition comprises less than 0.5% 4,4'-dihydroxy-3,3',5,5'-tetraisopropyl-biphenyl.

In one embodiment, the aqueous pharmaceutical composition comprises no more than 0.3% total impurities upon storage at 25° C. for 6 months.

In one embodiment, the aqueous pharmaceutical composition comprises 10 mg/mL of propofol and 175 mg/mL of sulfobutylether β-cyclodextrin, has a pH of about 5.5, and upon administration, the composition provides to a patient a dose-normalized propofol plasma $C_{24}$ of about 5 to about 8 (ng/mL)/(mg/kg).

In one embodiment, the aqueous pharmaceutical composition comprises 10 mg/mL of propofol and 175 mg/mL of sulfobutylether β-cyclodextrin, has a pH of about 5.5, and upon administration, the composition provides to a patient a dose-normalized propofol plasma $AUC_{0\text{-}24}$ of about 135 to about 450 (ng·h/mL)/(mg/kg).

In one embodiment, the aqueous pharmaceutical composition comprises 10 mg/mL of propofol and 175 mg/mL of sulfobutylether β-cyclodextrin, has a pH of about 5.5, and upon administration, the composition provides to a patient a dose-normalized propofol plasma $C_{24}$ of 6.24±1.78 (ng/mL)/(mg/kg) and a dose-normalized propofol plasma $AUC_{0\text{-}24}$ of 172±45 (ng·h/mL)/(mg/kg).

In one embodiment, the invention features a pharmaceutical composition comprising about 10 mg/mL of propofol, 175 mg/mL of sulfobutylether β-cyclodextrin, about 0.324 mg/mL citric acid, and water for injection, and has a pH of about 5.5. In one embodiment, the composition consists essentially of about 10 mg/mL of propofol, 175 mg/mL of sulfobutylether β-cyclodextrin, about 0.324 mg/mL citric acid, and water for injection, and has a pH of about 5.5. In another embodiment, the composition consists of about 10 mg/mL of propofol, 175 mg/mL of sulfobutylether β-cyclodextrin, about 0.324 mg/mL citric acid, and water for injection, and has a pH of about 5.5. In one embodiment, the sulfobutylether β-cyclodextrin in the composition is Captisol®.

In one embodiment, the invention features an aqueous pharmaceutical composition comprising 10 mg/mL of propofol, 175 mg/mL of Captisol®, a citric buffer, and has a pH of 5.5.

In one embodiment, a pharmaceutical composition of the present invention is administered to a patient to induce and/or maintain anesthesia or sedation, to initiate and/or maintain monitored anesthesia care sedation, or to induce and/or maintain intensive care unit sedation. The patient is a mammal, preferably a human.

In one embodiment, the invention features a process for manufacturing an aqueous pharmaceutical composition comprising dissolving propofol and sulfobutylether β-cyclodextrin in water, adding citric acid to the solution to adjust the pH to about 5.5, and sterile filtering the solution. In another embodiment, the composition is dispensed into a sterile vial, preferably a sterile glass vial. In a further embodiment, the solution is purged with nitrogen. In yet a further embodiment, 1 ml, 2 ml, 5 ml, 10 ml, 20 ml, 50 ml, or 100 ml of the composition is dispensed into a sterile vial.

In one embodiment, the invention features an aqueous pharmaceutical composition comprising 10 mg/mL of propofol, 175 mg/mL of Captisol®, and about 0.324 mg/mL citric acid, has a pH of 5.5, and when administered to a patient, the formulation provides the patient with an awakening time of 10 minutes or less. In one embodiment, the formulation provides the patient with an awakening time of 9, 8, 7, 6, or 5 minutes or less. In one embodiment, the composition provides a patient with a faster recovery from sedation compared to Diprivan®.

In one embodiment, the invention features an aqueous pharmaceutical formulation comprising 10 mg/mL of propofol, 175 mg/mL of Captisol®, and a citric buffer, wherein the composition has a pH of 5.5, and wherein the formulation is administered to a patient with a target-controlled infusion system.

In one embodiment, the invention features a method of inducing anesthesia or sedation in a patient in need thereof, the method comprising administering to said patient a pharmaceutical composition comprising 10 mg/mL of propofol, 175 mg/mL of sulfobutylether β-cyclodextrin, citric acid, and water for injection, wherein the composition has a pH of 5.5, and wherein the amount of propofol administered to the patient is in the range of 0.1 to 2.5 mg/kg to induce effective sedation or anesthesia. In another embodiment, the propofol is administered to the patient in a range of 0.125 to 2.0 mg/kg. In a further embodiment, the propofol is administered to the patient in an amount of 0.125, 0.25, 0.5, 1.0, 1.5, or 2.0 mg/kg.

In one embodiment, the invention features a method of maintaining anesthesia or sedation in a patient in need thereof, the method comprising administering to said patient a pharmaceutical composition comprising 10 mg/mL of propofol, 175 mg/mL of sulfobutylether β-cyclodextrin, citric acid, and water for injection, wherein the composition has a pH of 5.5, and wherein the propofol is administered to the patient at a rate of 2 to 6 mg/kg/h to maintain effective sedation or anesthesia.

In one embodiment, the invention features a method of initiating monitored anesthesia care sedation in a patient in need thereof, the method comprising administering to said patient a pharmaceutical composition consisting of 10 mg/mL of propofol, 175 mg/mL of sulfobutylether β-cyclodextrin, citric acid, and water for injection, wherein the composition has a pH of 5.5, and wherein the propofol is administered to the patient at a rate of 5 to 12 mg/kg/h to induce effective sedation or anesthesia.

In one embodiment, the invention features a method of maintaining monitored anesthesia care sedation in a patient in need thereof, the method comprising administering to said patient a pharmaceutical composition consisting of 10 mg/mL of propofol, 175 mg/mL of sulfobutylether β-cyclodextrin, citric acid, and water for injection, wherein the composition has a pH of 5.5, and wherein the propofol is administered to the patient at a rate of 1.2 to 4.5 mg/kg/h to maintain effective sedation or anesthesia.

In one embodiment, the invention features a method of initiating intensive care unit sedation in a patient in need thereof, the method comprising administering to said patient a pharmaceutical composition consisting of 10 mg/mL of propofol, 175 mg/mL of sulfobutylether β-cyclodextrin, citric acid, and water for injection, wherein the composition has a pH of 5.5, and wherein the propofol is administered to the patient at a rate of 0.1 to 2.5 mg/kg/h to induce effective sedation or anesthesia.

In one embodiment, the invention features a method of maintaining intensive care unit sedation in a patient in need thereof, the method comprising administering to said patient a pharmaceutical composition comprising 10 mg/mL of propofol, 175 mg/mL of sulfobutylether β-cyclodextrin, xx mg/mL citric acid, and water for injection, wherein the composition has a pH of 5.5, and wherein the propofol is administered to the patient at a rate of 0.1 to 3 mg/kg/h to maintain effective sedation or anesthesia.

In one embodiment, the invention features a pharmaceutical composition consisting of 10 mg/mL of propofol, 120 to 155 mg/mL of sulfobutylether β-cyclodextrin, citric acid, and water for injection, wherein the composition has a pH of 5.5.

In one embodiment, the invention features a pharmaceutical composition consisting of 10 mg/mL of propofol, 155 to 175 mg/mL of sulfobutylether β-cyclodextrin, citric acid, and water for injection, wherein the composition has a pH of 5.5.

In one embodiment, the invention features an aqueous pharmaceutical formulation comprising 10 mg/mL of propofol, 175 mg/mL of Captisol®, and a citric buffer, has a pH of about 5.5, and when administered to a patient, the formulation requires fewer dose adjustments compared to Diprivan® to maintain anesthesia or sedation.

Aqueous formulations disclosed herein have certain advantages over known propofol emulsions. For example, aqueous formulations of the present invention provide a lower blood concentration in a patient but maintain effective sedation and/or anesthesia, which would allow patients to recover from sedation more quickly compared to an emulsion, the formulations provide a lower dose variability and may be more quickly and accurately titrated compared to an emulsion, and they require a lower dose than an emulsion to induce and/or maintain effective sedation or anesthesia. The lower dose variability could also provide the advantage of a more accurate prediction of the required dose for a given patient before administration thereby reducing the need of dose titrate to achieve a given effect (e.g., inducing sedation quickly in a patient) as is required for Diprivan. In addition, compared to Diprivan, aqueous formulations disclosed herein have better compatibility with IV syringes, tubing, and in-line filters (e.g., less likely to clog syringes, tubing or filters). Microbial growth is less likely in formulations disclosed herein. Furthermore, it was surprisingly found that formulations disclosed herein with a pH of about 5.5 are more stable and subject to less degradation compared to a similar formulation with a higher pH (e.g., pH 6.5-7.0). For example, compared to a similar formulation with a high pH, propofol is less likely to become insoluble upon storage in the formulations disclosed herein. In addition, less degradation products (e.g., propofol dimmers) are formed after autoclave or fluorescence exposure in the disclosed formulations compared to similar a formulation with a high pH.

DETAILED DESCRIPTION OF THE INVENTION

One aspect of the invention is an aqueous pharmaceutical formulation comprising about 10 mg/mL propofol, 175 mg/mL sulfobutylether β-cyclodextrin, and has a pH in the range of between 4.5 and 6.5. In a preferred embodiment, the pH of the aqueous pharmaceutical formulation is about 5.5. It was surprisingly found at a pH of about 5.5, that the formulation is more stable and subject to less degradation compared to a similar formulation with a higher pH (e.g., pH 6.5-7.0).

In one embodiment, the aqueous pharmaceutical formulation comprises about 10 mg/mL propofol, 175 mg/mL sulfobutylether β-cyclodextrin, an acid, and has a pH of about 5.5. In one embodiment, the formulation comprises citric acid, preferably about 0.324 mg/mL citric acid. In a preferred embodiment, the formulation comprises 10 mg/mL propofol, 175 mg/mL sulfobutylether β-cyclodextrin, 0.324 mg/mL citric acid, and has a pH of 5.5. In a more preferred embodiment, the sulfobutylether β-cyclodextrin is sulfobutylether 7β-cyclodextrin, also known commercially as Captisol®.

Propofol has the structural formula of

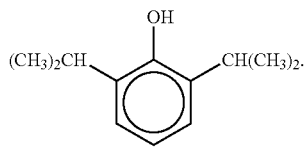

Propofol is a known anesthetic agent. The compound can be prepared by processes known in the art, for example, the compound can be prepared as described in U.S. Pat. Nos. 5,589,598, and 5,696,300. Propofol is also commercially available, for example, from BACHEM AMERICAS, INC., 3132 Kashiwa Street, Torrance, Calif. 90505, U.S.A.

Sulfobutylether β-cyclodextrin contained in the aqueous pharmaceutical formulation is a sulfobutylether derivative of beta-cyclodextrin. Cyclodextrins are cyclic carbohydrates that form truncated torodial structures with a hydrophilic exterior and lipophilic interior. Sulfobutylether β-cyclodextrin is soluble in water. It can form an inclusion complex with a hydrophobic chemical compound and increase the solubility of the compound.

Sulfobutylether β-cyclodextrin useful in the formulation typically has four to about seven sulfobutylether groups per cyclodextrin molecule. Sulfobutylether β-cyclodextrin can be prepared by methods known in the art, for example, as described in U.S. Pat. Nos. 5,376,645 and 5,134,127. It is also commercially available, for example, sulfobutylether β-cyclodextrin is sold under the name of Captisol®. Captisol®, also known as sulfobutylether 7β-cyclodextrin, has an average of about 6.5 sulfobutylether groups (range of 6.2 to 6.9) per cyclodextrin molecule. Captisol® can be prepared by methods known in the art, for example as described in U.S. Pat. No. 6,153,746. In one embodiment, the sulfobutylether 7β-cyclodextrin has an average molecular mass of 2163. In a preferred embodiment, the sulfobutylether β-cyclodextrin is sulfobutylether 7β-cyclodextrin. In a more preferred embodiment, the sulfobutylether β-cyclodextrin is Captisol®.

In one embodiment, the sulfobutylether β-cyclodextrin is present in the formulation in an amount of 120 to 175 mg/mL. In another embodiment, the sulfobutylether β-cyclodextrin is present in an amount of 120 to 155 mg/mL, preferably 120 to 145 mg/mL, more preferably 120 to 135 mg/mL. In yet another embodiment, the sulfobutylether β-cyclodextrin is present in an amount of 150 to 175 mg/mL, preferably 155 to 175 mg/mL, more preferably 160 to 175 mg/mL. The upper limit of the amount of sulfobutylether β-cyclodextrin in the formulation may be 175.1, 175.2, 175.3, 175.4, 175.5, 175.6, 175.7, 175.8, or 175.9 mg/mL.

The aqueous pharmaceutical formulation also comprises an acid to adjust the pH of the formulation. Non-limiting examples of acids include acetic acid, citric acid, phosphoric acid, ascorbic acid, tartaric acid, succinic acid, adipic acid, and malic acid. A few of these acids may act as chelating agents in the formulation. In a preferred embodiment, the acid is citric acid. In one embodiment, the pH of the aqueous composition is adjusted with a buffer. Examples of suitable buffers include, but are not limited to, an acetate buffer, a citrate buffer, a phosphate buffer, a lactate buffer, and a tartrate buffer. In a preferred embodiment, the pH is adjusted with a citrate buffer.

Formulations of the present invention may further comprise a preservative, an antioxidant, a tonicity modifier, an additional solubilizing agent, or a combination thereof.

Examples of suitable preservatives include, but are not limited to, 2-ethoxyethanol, 3-cresol, benzoic acid, benzyl alcohol, chlorbutanol, chlorhexidene, edetate sodium (EDTA), methylparaben, ethylparaben, propylparaben, butylparaben, phenol, phenoxyethanol, sodium metabisulfite, sorbic acid, and thimerosal, or combinations thereof.

Examples of suitable antioxidants include, but are not limited to, ascorbic acid, ascorbyl palmitate, butylated hydroxytoluene, butylated hydroxyanisole, propyl gallate, and tocopherols, or combinations thereof.

Examples of suitable tonicity modifiers include, but are not limited to, dextrose, glycerin, mannitol, potassium chloride, and sodium chloride, or combinations thereof.

Solubilizing agents increase the solubility of propofol in water. In addition to sulfobutylether β-cyclodextrin, one or more additional solubilizing agents may be included in the formulation. Examples of other suitable solubilizing agents include, but are not limited to, cyclodextrin derivatives such as hydroxypropyl beta cyclodextrin or 2-hydroxypropyl beta cyclodextrin, polysorbate 80 (Tween 80), polysorbate 20 (Tween 20), lecithin, polyoxyethylene-polyoxypropylene co-polymers (Pluronics), propylene glycol, glycerin, ethanol, polyethylene glycol (300 and 400), sorbitol, dimethylacetamide, and Cremophor EL.

The term "about" means that the number comprehended is not limited to the exact number set forth herein, and is intended to refer to ranges substantially within the quoted range while not departing from the scope of the invention. As used herein, "about" will be understood by persons of ordinary skill in the art to account for measurement errors, for example, in the range of up to plus or minus 10% of the particular term.

The aqueous pharmaceutical formulation may be prepared using methods known by one of ordinary skill in the art. In one embodiment, the sulfobutylether β-cyclodextrin is dissolved in water and then propofol is added to the solution. The solution is mixed for a period of time needed for the sulfobutylether β-cyclodextrin to fully solubilize the propofol. Citric acid is added in an amount to adjust the pH to about 5.5. The solution is sterile filtered, purged with nitrogen, and packaged in unit doses. Suitable filters for sterile filtration include filters having a pore size of 0.45 microns or less, preferably 0.22 microns or less. Alternatively, the solution is sterilized by autoclave.

The prepared and filter sterilized aqueous pharmaceutical formulation may be dispensed into suitable containers. Suitable containers for the packaging of these formulations include glass ampoules, vials or bottles; plastic bottles or bags; and pre-filled syringes. Light-resistant or light-proof containers, such as amber-colored glass bottles, may also be used. In one embodiment, the formulation may be packaged in single-use vials in volumes of 10 mL, 20 mL, 50 mL, or 100 mL. In a further embodiment, the 10 mL, 20 mL, 50 mL, or 100 mL vials may be packaged in kits of 10 vials per kit.

One of ordinary skill in the art will appreciate that formulations of the present invention are "ready to use" and may not require further dilution prior to administration. The formulations of the present invention do not require re-homogenization by shaking prior to administration. In one embodiment, the formulation may further be prepared in an isolated solid state for long-term storage by lyophilization, spray-drying, or other methods known to one of ordinary skill in the art.

The aqueous pharmaceutical formulation is stable upon preparation and storage. For example, the formulation is resistant to propofol degradation and propofol dimer (4,4'-dihydroxy-3,3',5,5'-tetraisopropyl-biphenyl) formation when stored at ambient conditions (e.g. 25° C. and 60% relative humidity). In one embodiment, the formulation contains no more than 0.5% 4,4'-dihydroxy-3,3',5,5'-tetraisopropyl-biphenyl. In one embodiment, the formulation contains no more than 1.0% total degradation impurities, preferably no more than 0.3% total degradation impurities.

Formulations of the present invention are also resistant to microbial growth without the addition of a preservative or antimicrobial agent. In one embodiment, the formulation provides for a no more than 10-fold increase in growth in each of *Staphylcoccus aureus* (ATCC 6538), *Escherichia coli* (ATCC 8739), *Pseudomonas aeruginosa* (ATCC 9027), *Candida albicans* (ATCC 10231), *Staphylcoccus epidermis* (ATCC 12228), and *Aspergillus niger* (ATCC 16404) for at least 6 months to 2 years when stored at 25° C. and 60% relative humidity The aqueous pharmaceutical formulation is suitable for use in the induction and maintenance of anesthesia or sedation in a patient. In one embodiment, the aqueous pharmaceutical formulation is administered to a patient for the initiation and maintenance of monitored anesthesia care (MAC) sedation. In another embodiment, the aqueous pharmaceutical formulation is administered to a patient for the induction and/or maintenance of general anesthesia. In a further embodiment, the aqueous pharmaceutical formulation is administered to a patient for Intensive Care Unit (ICU) sedation of intubated, mechanically ventilated patients. Intermittent boluses of the formulation may also be required to maintain effective sedation. The formulation may also be used for Emergency Department Procedural Sedation in situations where sedatives or analgesics are administered during brief, painful procedures (e.g. fracture or dislocation reduction, abscess incision and drainage, wound care, etc.).

In one embodiment, the formulation is administered to a patient via intravenous infusion. When administering the formulation by infusion, a syringe or volumetric pump may be used to provide controlled infusion rates. In another embodiment, the formulation is administered to a patient using a target-controlled infusion system. One of ordinary skill in the art will also understand that formulations of the present invention could be co-administered with other pharmaceutically acceptable active agents, either simultaneously or sequentially. In one embodiment, nitrous oxide may be co-administered with the aqueous propofol formulation to provide satisfactory anesthesia. In another embodiment, the formulation may be used with additional agents such as atropine, scopolamine, glycopyrrolate, diazepam, depolarizing and nondepolarizing muscle relaxants, and opioid analgesics, as well as with inhalational and regional anesthetic agents. In a further embodiment, the aqueous propofol formulation may be co-administered with fentanyl, alfentanil, or sufentanil. In yet another embodiment, the formulation may be co-administered with lidocaine.

The patient being administered with the formulation can be a mammal. In a preferred embodiment, the patient is a human.

Dosages of propofol in the present invention to induce or maintain sedation or anesthesia typically range from about 0.05 to about 15 mg/kg, preferably from 0.05 to 7 mg/kg. In one embodiment, the dosage of propofol ranges from 0.05 to 2 mg/kg, preferably from about 0.1 to about 2 mg/kg, more preferably from about 0.125 to about 2 mg/kg. For example, the propofol dosage may be about 0.125, about 0.25, about 0.5, about 1.0, about 1.5, or about 2.0 mg/kg. In another embodiment, the dosage ranges from 0.7 to 1.5 mg/kg, preferably from 0.7 to 1.2 mg/kg. In a further embodiment, the dosage of propofol ranges from 0.7 to 2.0 mg/kg, preferably from 0.7 to 1.7 mg/kg. One advantage of formulations of the current invention is that they can provide effective sedation or anesthesia at a lower dose compared to Diprivan®.

In one embodiment, the dosage of propofol ranges from 1.7 to 2.5 mg/kg, preferably from 1.7 to 2.2 mg/kg. In an additional embodiment, the dosage of propofol ranges from 2 to 5 mg/kg, preferably from 2 to 4 mg/kg. In one embodiment, the dosage of propofol ranges from 8 to 15 mg/kg, preferably from 8 to 12 mg/kg, more preferably from 8 to 10 mg/kg.

Administration rates of propofol to induce or maintain anesthesia typically vary from 0.05 to 20 mg/kg/h. In one embodiment, the administration rate of propofol ranges from 0.2 to 18 mg/kg/h, preferably 1.2 to 4.5 mg/kg/h, more preferably 2 to 6 mg/kg/h. In another embodiment, the administration rate ranges from 4 to 12 mg/kg/h, preferably from 5 to 12 mg/kg/h, more preferably from 5 to 9 mg/kg/h. In a further embodiment, the administration rate ranges from 6.5 to 18 mg/kg/h, preferably from 6.5 to 16 mg/kg/h. In one embodiment, the administration rate ranges from 20 to 42 mg/kg/h.

In one embodiment, the administration rate of propofol ranges from 0.05 to 3 mg/kg/h, preferably from 0.05 to 0.3 mg/kg/h. In another embodiment, the administration rate ranges from 0.1 to 6 mg/kg/h, preferably from 0.1 to 5 mg/kg/h, more preferably 0.1 to 3 mg/kg/h, and even more preferably 0.1 to 2.5 mg/kg/h. One advantage of formulations of the current invention is that they provide effective sedation or anesthesia at a lower administration rate compared to Diprivan®.

Intermittent boluses may be administered to patients to maintain general anesthesia or monitored anesthesia care sedation at propofol doses ranging from 5 to 50 mg, preferably 10 to 40 mg. Intermittent boluses may also be administered with nitrous oxide to patients undergoing general surgery in a propofol dosage range of 5 to 50 mg, preferably 10 to 40 mg. One skilled in the art would understand that these intermittent boluses should be administered when changes in vital signs indicate a response to surgical stimulation or light anesthesia.

One of ordinary skill in the art would understand the need to modify the dose or administration rate of propofol to induce effective sedation or anesthesia on an individual basis. For example, one skilled in the art may use a bispectral index monitor to evaluate the effective depth of anesthesia or sedation in a patient. One skilled in the art may also adjust the propofol dose or administration rate until a surgical plane of anesthesia was achieved, for example, a level of anesthesia was maintained between plane 1 (most reflexes still present) and plane 2 (medium anesthesia; most surgeries are conducted at this level; muscles relaxed and most reflexes absent) as determined using Guedel's classification.

The anesthesia and sedation effects of the aqueous pharmaceutical formulation disclosed herein were tested in animal studies and compared to commercially available emulsion products such as Diprivan®. The dose of the aqueous pharmaceutical formulation for inducing and maintaining anesthesia or sedation is comparable to that of Diprivan®. However, it was unexpectedly found that the plasma propofol concentrations provided by the aqueous pharmaceutical formulation disclosed herein were significantly lower than that of Diprivan® while maintaining effective sedation and anesthesia. In one embodiment, the aqueous propofol formulation provides a plasma propofol concentration that is 40-50% lower than that of Diprivan®. In one embodiment, the aqueous formulation provides fewer side effects in patients.

The results from the animal studies also suggest that patients administered with the aqueous pharmaceutical formulation would have a faster recovery time compared to Diprivan®. Therefore, in one aspect, the invention provides an aqueous pharmaceutical formulation comprising 10 mg/mL of propofol, 175 mg/mL of sulfobutylether β-cyclodextrin, and a citric buffer, wherein the composition has a pH of 5.5, and wherein when administered to a patient, the formulation provides for an awakening time of 10 minutes or less. In one embodiment, the formulation provides the patient with an awakening time of 9, 8, 7, 6, or 5 minutes or less. In one embodiment, when administered to a patient, the composition provides the patient a faster recovery from sedation compared to Diprivan®.

Propofol levels in a patient need to be monitored and adjusted to maintain anesthesia or sedation of the patient. In the animal studies, it was also unexpectedly found that variations in propofol levels provided by the aqueous pharmaceutical formulation were statistically significantly lower than that of Diprivan®. This result suggests that the aqueous pharmaceutical formulation would require fewer dose adjustments to maintain anesthesia or sedation in a patient. Thus, in one aspect, the invention provides an aqueous pharmaceutical formulation comprising 10 mg/mL of propofol, 175 mg/mL of sulfobutylether β-cyclodextrin, and a citric buffer, wherein the composition has a pH of 5.5, and wherein when administered to a patient, the formulations require fewer dose adjustments compared to Diprivan® for maintaining anesthesia or sedation.

The following non-limiting examples further illustrate the present invention.

EXAMPLES

Example 1

| Ingredient | Amount (mg/mL) |
| --- | --- |
| Propofol | 10 |
| Sulfobutylether β-cyclodextrin (e.g. Captisol ®) | 175 |
| Sodium citrate dihydrate | 1.017 |
| Citric acid hydrate | 0.324 |
| Water for injection | q.s. |

17.5 g of sulfobutylether β-cyclodextrin was dissolved in water and then 10 g of propofol was added to the solution. The solution was mixed for a period of time needed for the sulfobutylether β-cyclodextrin to fully solubilize the propofol. Sodium citrate dihyate and citric acid hydrate were added in an amount to adjust the pH to 5.5 and water for injection was added to make the volume to 100 mL. The solution was sterile filtered with a 0.22 μm-pore filter, dispensed into sterile glass vials, and the purged with nitrogen. Alternatively, the solution was sterilized by autoclave. Each of the components can be scaled up or down proportionally to make a desired amount of the formulation.

Example 2

2 separate groups of 6 companion beagle dogs (3 males and 3 females in each group) were given a bolus injection followed by a 24 hr infusion of either the formulation as prepared in Example 1 ("test formulation") or Diprivan ("reference formulation"). The doses were titrated until a surgical plane of anesthesia was achieved. The rate of infusion was continuously adjusted to maintain a level of anesthesia between plane 1 (most reflexes still present) and plane 2 (medium anesthesia; most surgeries are conducted at this level; muscles relaxed and most reflexes absent) such that each animal was unconscious and immobile. Additional bolus doses were administered and rates were adjusted to achieve this level of anesthesia at the discretion of the surgeon. Blood samples were taken before the start of infusion and 0.25, 12 and 24 hours after the start of infusion for the subjects receiving the test formulation, and before the infusion and 24 hours after the start of the infusion for subjects receiving the reference formulation. Results from the analysis of propofol in the blood samples are shown in Table 1 and Table 2, respectively.

TABLE 1

Propofol plasma results after administration with test formulation

| Subject | Actual Dose (mg/kg) | $C_{24}$ (ng/mL) | $AUC_{0-24}$ | $C_{24}$/Dose (ng/mL)/(mg/kg) | $AUC_{0-24}$/Dose (ng · h/mL)/(mg/kg) | $CL^a$ (mL/h/kg) | $V_z^a$ (L/kg) |
| --- | --- | --- | --- | --- | --- | --- | --- |
| 4501 | 848 | 4,690 | 140,000 | 5.53 | 165 | 5430 | 28.2 |
| 4502 | 732 | 5,710 | 144,000 | 7.80 | 197 | 4590 | 25.7 |
| 4503 | 842 | 5,310 | 116,000 | 6.31 | 138 | 6710 | 32.8 |
| 4001 | 776 | 5,123 | 152,000 | 6.60 | 196 | 4560 | 33.6 |
| 4002 | 654 | 3,770 | 105,000 | 5.76 | 161 | 5790 | 19.0 |
| 4003 | 766 | 4,170 | 135,000 | 5.44 | 176 | 5160 | 22.0 |

TABLE 1-continued

Propofol plasma results after administration with test formulation

| Subject | Actual Dose (mg/kg) | $C_{24}$ (ng/mL) | $AUC_{0-24}$ | $C_{24}$/Dose (ng/mL)/(mg/kg) | $AUC_{0-24}$/Dose (ng · h/mL)/(mg/kg) | $CL^a$ (mL/h/kg) | $V_z^a$ (L/kg) |
|---|---|---|---|---|---|---|---|
| Mean | 770 | 4,800 | 131,000 | 6.24 | 172 | 5173 | 26.9 |
| SD | 72.4 | 729 | 23,800 | 0.89 | 22.6 | 810 | 5.8 |
| CV % | 9.4 | 15.2 | 18.2 | 14.2 | 13.1 | 15.1 | 21.6 |

$^a$CL and $V_z$ values calculated from estimated $t_{1/2}$ values.
$C_{24}$ = blood plasma concentration at 24 hours from the start of infusion;
$AUC_{0-24}$ = area under the blood plasma concentration-time curve from time 0 to 24 hours after the start of infusion;
CL = systemic clearance;
SD = standard deviation;
CV = coefficient of variable;
$V_z$ = volume of distribution in the terminal phase

TABLE 2

Propofol plasma results after administration with reference formulation

| Subject | Actual Dose (mg/kg) | $C_{24}$ (ng/mL) | $AUC_{0-24}$ | $C_{24}$/Dose (ng/mL)/(mg/kg) | $AUC_{0-24}$/Dose (ng · h/mL)/(mg/kg) | $CL^a$ (mL/h/kg) | $V_z^a$ (L/kg) |
|---|---|---|---|---|---|---|---|
| 3501 | 733 | 6,700 | 201,000 | 9.14 | 274 | 3390 | 21.4 |
| 3502 | 1107 | 11,700 | 246,000 | 10.6 | 222 | 4150 | 21.7 |
| 3503 | 923 | 10,700 | 210,000 | 11.6 | 228 | 3860 | 26.9 |
| 3001 | 479 | 6,160 | 197,000 | 12.9 | 411 | 2270 | 13.1 |
| 3002 | 755 | 9,530 | 197,000 | 12.6 | 261 | 3500 | 25.6 |
| 3003 | 899 | 13,000 | 272,000 | 14.5 | 303 | 3040 | 22.6 |
| Mean | 816 | 9,630 | 221,000 | 11.9 | 283 | 3368 | 21.9 |
| SD | 213 | 2,740 | 31,300 | 1.87 | 69.4 | 661 | 4.8 |
| CV % | 26.1 | 28.4 | 14.2 | 15.7 | 24.5 | 19.6 | 22.1 |

$^a$CL and $V_z$ values calculated from estimated $t_{1/2}$ values.
$C_{24}$ = plasma concentration at 24 hours from the start of infusion;
$AUC_{0-24}$ = area under the plasma concentration-time curve from time 0 to 24 hours after the start of infusion;
SD = standard deviation;
CV = coefficient of variable;
CL = systemic clearance;
$V_z$ = volume of distribution in the terminal phase While the actual mean dose was similar between the test and reference formulations (770 mg/kg vs. 816 mg/kg), dose-normalized $C_{24}$ and $AUC_{0-24}$ levels of the test formulation were roughly 40-50% lower than those of the reference formulation. Despite this fact, effective sedation was maintained with the test formulation. The mean systemic clearance for the test formulation was about 35% higher than the reference systemic clearance. These findings were surprising because there had not been any reason to believe that the aqueous formulation would provide a substantially lower plasma concentration while providing sedation or anesthesia comparable to the reference formulation. Also, the volume of distribution of the test formulation was roughly 20% higher than that of the reference formulation.

The intersubject actual dosage variability for the test and reference formulations was 9.4% vs. 26.1%. The difference between the variability of the test and reference formulations is statistically significant. This result is also surprising because there had been no indication that the aqueous formulation would provide a lower dosage variability compared to the reference formulation. This suggests that the test formulation could be titrated more accurately and reliably from patient to patient than the reference formulation and requires fewer dose adjustments compared to the reference formulation. This would make the test formulation more preferable when using a target-controlled infusion system.

A person of ordinary skill in the art would appreciate that the propofol dosages administered in the above animal study may be used to derive human equivalent dosages using methods known in the art. For example, human equivalent doses may be derived from animal doses using methods described in the FDA Guidance: Estimating the Maximum Safe Starting Dose in Initial Clinical Trials for Therapeutics in Adult Healthy Volunteers, published on Jul. 6, 2005, which is incorporated herein by reference in its entirety.

What is claimed is:

1. An aqueous pharmaceutical composition comprising 10 mg/mL of propofol, 175 mg/mL of sulfobutylether β-cyclodextrin, a citrate buffer, and water for injection.

2. The aqueous pharmaceutical composition of claim 1, wherein the sulfobutylether β-cyclodextrin is sulfobutylether 7β-cyclodextrin.

3. An aqueous pharmaceutical composition according to claim 1, wherein the composition further comprises a preservative, an antioxidant, a tonicity modifier, an additional solubilizing agent, or a combination thereof.

4. The aqueous pharmaceutical composition of claim 1, wherein the composition comprises less than 0.5% 4,4'-dihydroxy-3,3',5,5'-tetraisopropyl-biphenyl.

5. The aqueous pharmaceutical composition of claim 1, wherein the composition comprises no more than 0.3% total degradation impurities upon storage at 25° C. for 6 months.

6. A method of inducing and/or maintaining anesthesia or sedation in a patient in need thereof, the method comprising administering to the patient the pharmaceutical composition of claim 1.

7. A method of inducing and/or maintaining monitored anesthesia care sedation in a patient in need thereof, the method comprising administering to the patient a pharmaceutical composition of claim 1.

8. A method of inducing and/or maintaining intensive care unit sedation in a patient in need thereof, the method comprising administering to the patient a pharmaceutical composition of claim 1.

9. The method of claim 6, wherein the propofol is administered at a rate of from about 0.05 mg/kg/h to about 20 mg/kg/h.

10. A method of inducing anesthesia or sedation in a patient in need thereof, the method comprising administering to said patient a pharmaceutical composition comprising about 10 mg/mL of propofol, 175 mg/mL of sulfobutylether β-cyclodextrin, a citrate buffer, and water for injection, and wherein the amount of propofol administered to the patient is in the range of about 0.125 mg/kg to about 2.0 mg/kg to induce effective sedation or anesthesia.

11. A method of maintaining anesthesia or sedation in a patient in need thereof, the method comprising administering to said patient a pharmaceutical composition comprising about 10 mg/mL of propofol, 175 mg/mL of sulfobutylether β-cyclodextrin, a citrate buffer, and water for injection, and wherein the propofol is administered to the patient at a rate of about 2 mg/kg/h to about 6 mg/kg/h to maintain effective sedation or anesthesia.

12. The aqueous pharmaceutical composition of claim 1, wherein upon administration, the composition provides to a patient a dose-normalized propofol plasma $C_{24}$ of about 5 to about 8 (ng/mL)/(mg/kg).

13. The aqueous pharmaceutical composition of claim 1, wherein the composition has a pH of about 5.5.

14. The aqueous pharmaceutical composition of claim 1, wherein when administered to a patient, the composition provides the patient with an awakening time of 10 minutes or less.

15. The method according to claim 10, wherein the sulfobutylether β-cyclodextrin is sulfobutylether 7β-cyclodextrin.

16. The method according to claim 11, wherein the sulfobutylether β-cyclodextrin is sulfobutylether 7β-cyclodextrin.

17. The method according to claim 10, wherein the composition has a pH of about 5.5.

18. The method according to claim 11, wherein the composition has a pH of about 5.5.

19. The method of claim 7, wherein the propofol is administered at a rate of from about 0.05 mg/kg/h to about 20 mg/kg/h.

20. The method of claim 8, wherein the propofol is administered at a rate of from about 0.05 mg/kg/h to about 20 mg/kg/h.

* * * * *